United States Patent
Pack et al.

(10) Patent No.: US 8,948,337 B2
(45) Date of Patent: Feb. 3, 2015

(54) COMPUTED TOMOGRAPHY IMAGE RECONSTRUCTION

(71) Applicant: General Electric Company, Schenectady, NY (US)

(72) Inventors: Jed Douglas Pack, Glenville, NY (US); Kai Zeng, Clifton Park, NY (US); Adam Budde, Madison, WI (US)

(73) Assignee: General Electric Company, Niskayuna, NY (US)

( * ) Notice: Subject to any disclaimer, the term of this patent is extended or adjusted under 35 U.S.C. 154(b) by 145 days.

(21) Appl. No.: 13/793,669

(22) Filed: Mar. 11, 2013

(65) Prior Publication Data

US 2014/0254905 A1  Sep. 11, 2014

(51) Int. Cl.
*G01N 23/04* (2006.01)
*G06T 7/00* (2006.01)

(52) U.S. Cl.
CPC ............ *G06T 7/0012* (2013.01); *G01N 23/046* (2013.01)
USPC .............................................. 378/4; 382/131

(58) Field of Classification Search
USPC ................... 378/4, 19, 62; 382/131
See application file for complete search history.

(56) References Cited

U.S. PATENT DOCUMENTS

| | | | |
|---|---|---|---|
| 5,253,171 A * | 10/1993 | Hsiao et al. | 378/4 |
| 6,219,441 B1 | 4/2001 | Hu | |
| 6,990,167 B2 * | 1/2006 | Chen | 378/4 |
| 7,424,088 B2 | 9/2008 | Zamyatin et al. | |
| 7,444,011 B2 * | 10/2008 | Pan et al. | 382/131 |
| 7,447,295 B2 * | 11/2008 | Hoheisel et al. | 378/4 |
| 7,643,605 B2 | 1/2010 | Ning et al. | |
| 8,284,892 B2 | 10/2012 | Pack et al. | |
| 2005/0175144 A1 | 8/2005 | Hsieh | |
| 2006/0165271 A1 | 7/2006 | Fischer et al. | |
| 2006/0198491 A1 | 9/2006 | Taguchi | |

* cited by examiner

Primary Examiner — Irakli Kiknadze
(74) Attorney, Agent, or Firm — Robert M. McCarthy

(57) ABSTRACT

Approaches for performing computed tomographic image reconstruction are described. In one embodiment, a full or almost full scan of scan data is acquired and a plurality of image reconstructions are performed based on the scan data, wherein the plurality of image reconstructions result in a corresponding plurality of image volumes wherein the image reconstructions use different view weighting functions. Further, the present approaches provide for combining the plurality of image volumes together to produce a final image volume.

21 Claims, 9 Drawing Sheets

COMPUTED TOMOGRAPHY IMAGE RECONSTRUCTION

BACKGROUND

Embodiments of the invention generally relate to imaging, and more particularly to reconstruction of computed tomography data.

In a typical computed tomography (CT) system, an X-ray source projects a fan-shaped or cone-shaped beam, which is collimated to lie within an X-Y plane of a Cartesian coordinate system termed the "imaging plane." The X-ray beam passes through an object being imaged, such as a medical patient, and is incident upon an array of radiation detectors. The detector array includes detector elements, each of which measures the intensity of transmitted radiation along a beam projected from the X-ray source to the particular detector element. The intensity of the transmitted radiation is dependent upon the attenuation of the X-ray beam by the object and each detector produces a separate electrical signal that is a measurement of the beam attenuation. The signals are processed and reconstructed to form images which may be evaluated themselves or which may be associated to form a volume rendering or other representation of the imaged region. In a medical context, pathologies or other structures of interest may then be located or identified from the reconstructed or rendered volume.

During the past few years, the use of cone-beam tomography has become more prevalent. Various techniques that allow accurate reconstruction for many different source trajectories (such as helix, saddles, variable pitch helix, circle-plus-arc, and so forth) have been developed. Progress has also been made on developing algorithms for trajectories that do not satisfy Tuy's completeness condition everywhere in the imaging volume such as for the circular trajectory and for the circular segment trajectory. These trajectories satisfy Tuy's condition only at certain points within a single plane, yet data acquired along these paths may be used to reconstruct volumetric data, resulting in reconstructed images that may exhibit cone-beam artifacts.

Cone-beam artifacts degrade the quality of the reconstructed CT images. Moreover, as CT scanners evolve to larger coverage, such artifacts may become more problematic. For example, cone-beam artifacts produce shading and glaring around high contrast edges in CT images. These artifacts are undesirable and may sometimes affect the quantitative robustness of CT numbers. Moreover, conventional techniques fail to provide desired imaging quality due to cone-beam artifacts. Also, use of other currently available techniques result in new artifacts being introduced due to data truncation, additional interpolation and filtering. Further, traditional techniques of cone-beam reconstruction use weighting of different parts of the data by different amounts that result in high computational cost and time.

It is therefore desirable to provide an efficient and computationally less intensive reconstruction technique and to reduce cone-beam artifacts in CT images without compromising on image quality.

BRIEF DESCRIPTION

In one embodiment, a method of reconstructing a computed tomography (CT) image is provided. In accordance with an embodiment of this method, a set of projection data is acquired for an imaged volume using a CT imaging system. At least a first intermediate reconstruction and a second intermediate reconstruction are reconstructed using the acquired set of projection data. The first intermediate reconstruction and the second intermediate reconstruction are reconstructed using different view weightings. The first intermediate reconstruction and the second intermediate reconstruction are masked to select different subdivisions of image data. A frequency transform is applied to transform each subdivision of image data to frequency space. The frequency transform of each subdivision is masked to select frequency information of interest for each of the first intermediate reconstruction and the second intermediate reconstruction. For each subdivision, the frequency information selected from the first intermediate reconstruction is combined with the frequency information selected from the second intermediate reconstruction to generate a fully sampled frequency space. An inverse frequency transform is applied to the fully sampled frequency space to generate a final image volume.

In a further embodiment, a non-transitory, computer-readable medium configured to store one or more routines executable by a processing system is provided. The routines, when executed, causing acts to be performed comprising: accessing a set of axial CT projection data; reconstructing a first intermediate reconstruction using the set of axial CT projection data and a first view weighting; reconstructing a second intermediate reconstruction using the set of axial CT projection data and a second view weighting that differs from the first view weighting; selecting, from the first intermediate reconstruction and the second intermediate reconstruction, a plurality of subdivisions of data corresponding to different portions of a final image to be reconstructed; transforming the plurality of subdivisions of data into corresponding frequency representations; masking the frequency representations to select frequency information of interest for each of the first intermediate reconstruction and the second intermediate reconstruction; combining the selected frequency information from the first intermediate reconstruction and the second intermediate reconstruction to generate a fully sampled frequency space for each subdivision; and applying an inverse frequency transform to the fully sampled frequency space to generate the final image.

In an additional embodiment, a computed tomography (CT) imaging system is provided. The CT imaging system comprises a source of X-ray emissions and a detector positioned opposite from the source with respect to an imaging volume. The detector is configured to generate signals in response to the X-rays, when emitted. The CT imaging system further comprises a rotational positioning system configured to rotate the source and the detector about the imaging volume and a detector acquisition system configured to acquire the signals generated by the detector. In addition, the CT imaging system comprises a memory storing one or more routines and a processing component configured to access the signals from the data acquisition system and to execute the one or more routines stored in the memory. The one or more routines, when executed by the processing component, cause acts to be performed comprising: reconstructing at least a first intermediate reconstruction and a second intermediate reconstruction using the signals acquired by the detector acquisition system, wherein the first intermediate reconstruction and the second intermediate reconstruction are reconstructed using different view weightings; dividing the first intermediate reconstruction and the second intermediate reconstruction into corresponding subdivisions of data; applying a fast Fourier transform to transform each subdivision of image data to frequency representations; combining selected frequency information from the first intermediate reconstruction with the selected frequency information from the second intermediate reconstruction to generate a fully sampled frequency space for each subdivision; and applying an inverse fast Fourier transform to the fully sampled frequency space to generate a final image volume.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments disclosed herein provide algorithms for the reconstruction of images from data collected using cone-beam computed tomography (CT). The algorithms address artifacts attributable to one or more of truncation of data in the z-direction, mishandled data due to incorrect weighting of data redundancy, and/or missing frequency data. The approaches disclosed herein may be suitable for use with a range of tomographic reconstruction systems. To facilitate explanation, the present disclosure will primarily discuss the present reconstruction approaches in the context of a CT system. However, it should be understood that the following discussion may also be applicable to other tomographic reconstruction systems.

Figure 1:
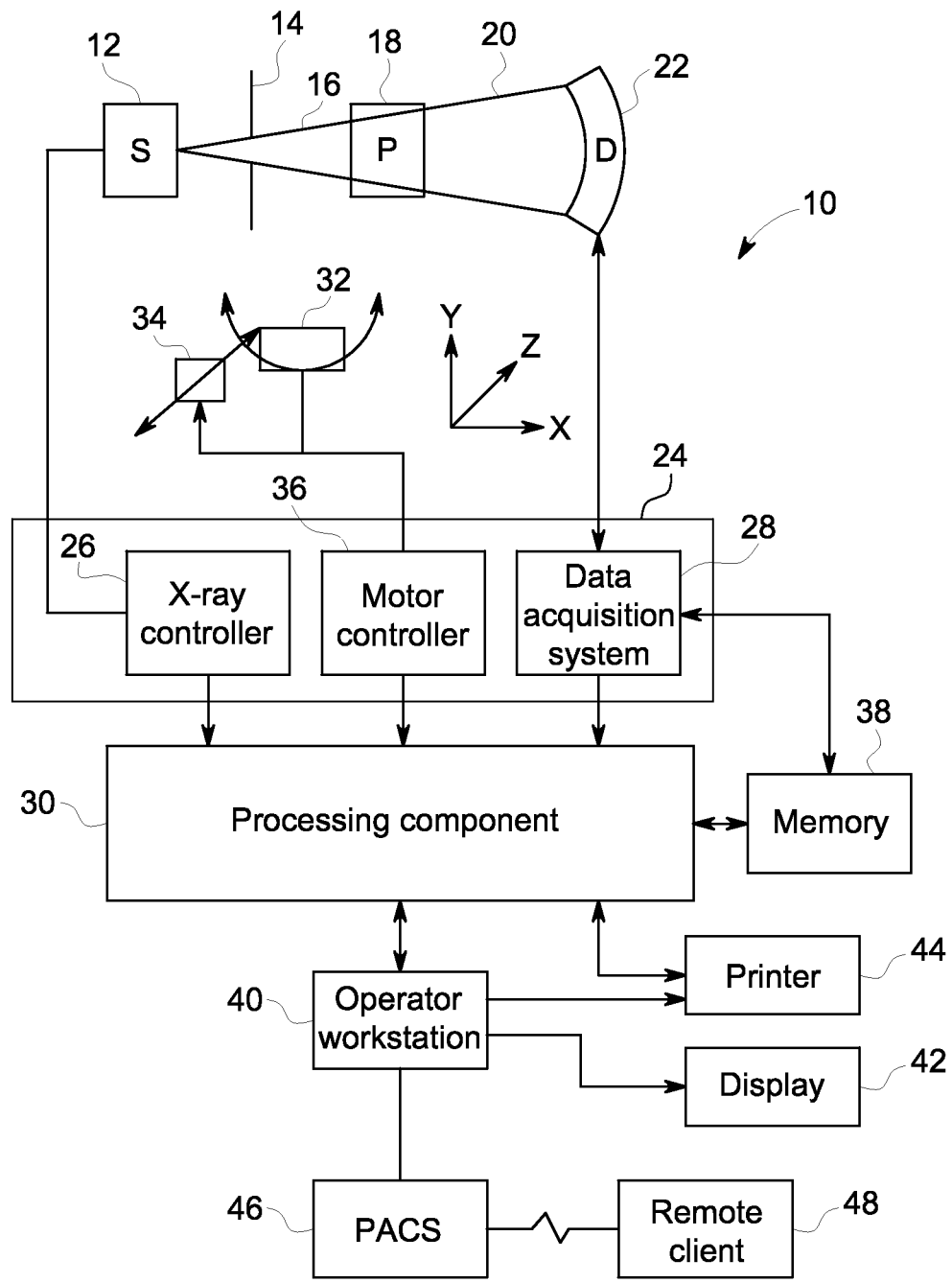
FIG. 1 is a diagrammatical view of a CT imaging system for use in producing images, in accordance with aspects of the present disclosure.

With this in mind, an example of a computer tomography (CT) imaging system 10 designed to acquire X-ray attenuation data at a variety of views around a patient (or other subject or object of interest) and suitable for tomographic reconstruction is provided in FIG. 1. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to be a cone-shaped beam, i.e., a cone-beam, that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18.

Source 12 is controlled by a system controller 24, which furnishes both power, and control signals for CT examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x,y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols and to process acquired data. For example, the system controller 24, via the systems and controllers noted above, may rotate a gantry supporting the source 12 and detector 22 about a subject of interest so that X-ray attenuation data may be obtained at a variety of views relative to the subject. In the present context, system controller 24 may also includes signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

As noted above, the reconstruction of images from data acquired by an imaging system, such as the depicted CT imaging system 10, may be subject to various limitations that may result in artifacts or other imperfections in the generated images. For example, the acquired data may be truncated in the z-direction (i.e., longitudinal direction) in certain acquisition scenarios. In particular, in an axial (i.e., circular) cone-beam acquisition, certain of the voxels in the image volume will always be in the X-ray beam during the axial spin (such as those voxels near the mid-plane i.e., plane in which the X-ray focal spot moves) while other voxels are illuminated in certain of the views during the axial spin but not in others. For example, due to the narrow portion of the X-ray cone being closer to the X-ray source 12, (that is, the cone expands or diverges as distance from the source increases) a narrow segment of voxels near the X-ray 12 source may be illuminated while those voxels furthest from the source are fully or mostly illuminated due to being near the wide base of the cone. However, as the X-ray source is rotated axially about the volume, the portions of the volume that are near and far from the X-ray source 12 will also rotate, with the result being that the extent of X-ray illumination a voxel receives may decay monotonically with distance of the voxel from the mid-plane of focal spot rotation. As a result, there is less data available with respect to the edges of the X-ray cone in the z-direction in an axial scan than for those voxels nearer the mid-plane of the cone in the z-direction. This data truncation in the z-direction may prevent the reconstruction of good quality images outside that portion of the volume which is always projected onto the detector during an axial scan, leading to cone-beam artifacts.

In the case of mishandled frequencies, any given voxel will be seen by the source and detector for a certain angular view range in a given cone-beam axial scan. However, some Radon directions or frequencies may be unevenly sampled, which effectively occurs when some projections miss the detector. Thus, some frequencies may be measured twice in such a scan, compared to other frequencies that are measured once. The reconstruction should correctly take into account this uneven sampling of frequency space or artifacts may result. Simple sinogram domain weighting may not always meet this goal accurately and therefore more advanced filtering techniques may be useful. In certain instances, mishandled data as described herein may result in cone-beam artifacts in the reconstructed image.

In addition, in some instances where a cone-beam axial scan is employed, certain frequency information may be missing for a given voxel. For example, even inside the 360 degree region generated by a circular (i.e., axial) scan, there may be some missing frequencies, particularly along the z-direction. The amount of missing frequencies will increase with distance from the mid-plane (plane in which the x-ray focal spot moves).

With the foregoing discussion of systems and potential imaging issues in mind, the following discussion relates to algorithms that may be used to address certain of these issues in the reconstruction of CT images. Unless indicated otherwise, the algorithms and processing steps discussed below are implemented after a fan-to-parallel rebinning step in the image reconstruction flow. Therefore, the projections and views discussed herein are in the parallel projection space. As will be appreciated, however, the rebinning step is not necessary and, in other implementations, this rebinning step may not be performed.

In general, during a CT cone-beam data acquisition, the number of views that have a projection that hits off of the detector 22 will increase as you move away from the center slice in the Z-direction (i.e., along the axial bore) or away from the center of the field of view in the XY-plane orthogonal to the Z-axis. Thus the number of views that project onto the detector 22 can decrease from a full scan of data in the region of good data (i.e., a full set of good projections, where the projections impact the detector at all angles) to less than a half scan of data in the regions or corners away from the region of good data (i.e., where the detector 22 is not impacted by projections through a voxel at all angles). The algorithms discussed herein provide a benefit when, at a given voxel, a portion of the view's projections hit off of the detector, resulting in data insufficiency.

Figure 2:
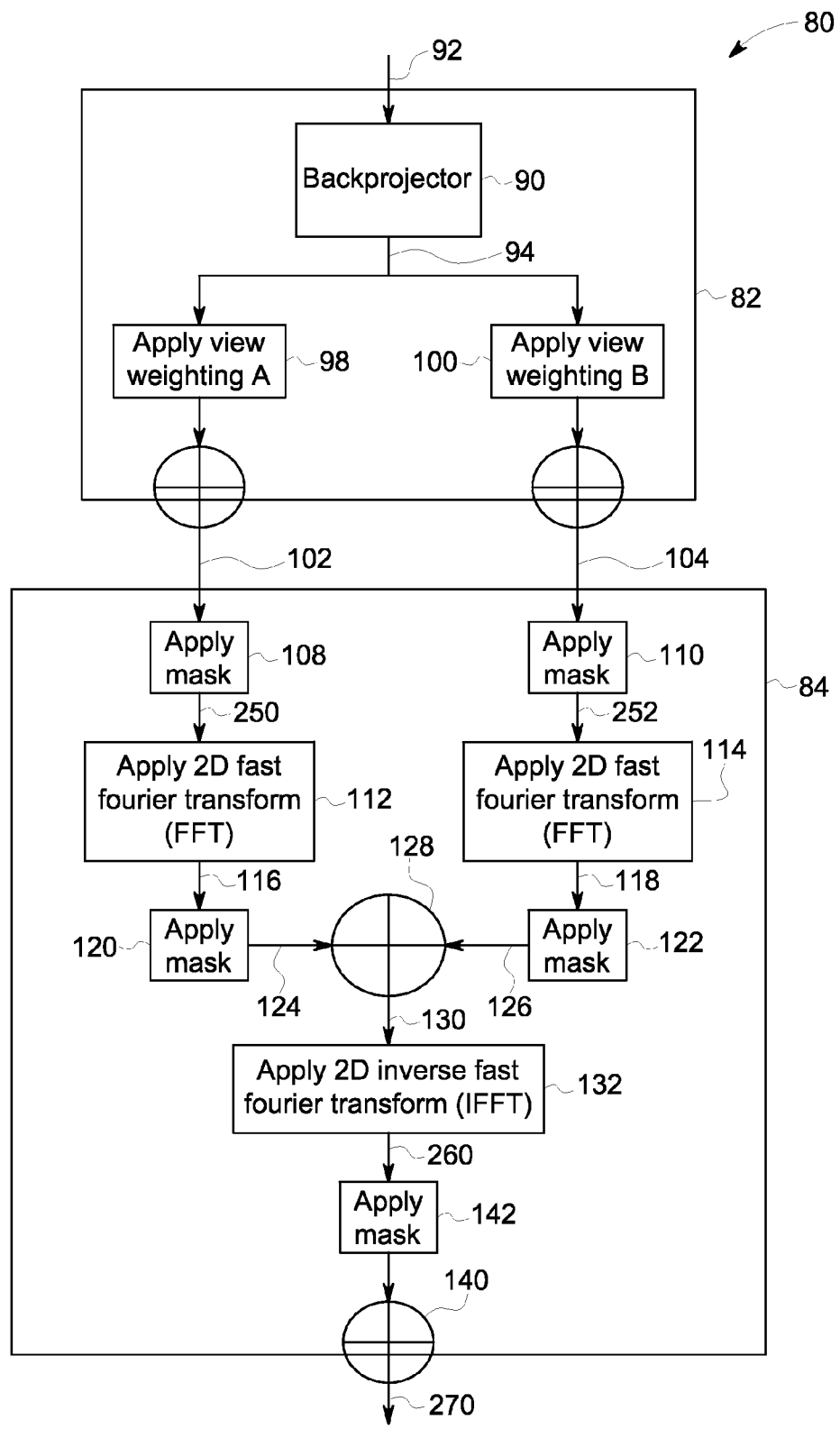
FIG. 2, depicts control flow logic describing an embodiment of an algorithm for reconstructing an image, in accordance with aspects of the present disclosure.

Turning to FIG. 2, a generalized flow diagram corresponding to control logic of an algorithm 80 for processing projection data in accordance with one embodiment is depicted. In accordance with the depicted implementation a first set 82 of steps are performed at each view while a second set 84 of subsequent steps are performed at each subdivision of data, as discussed below. In particular, for each view, backprojection (block 90) is performed to a set of sinogram data 92 derived from a data acquisition for the respective view. The image 94 thereby generated is view weighted (blocks 98, 100), as discussed herein, using different weights (e.g., view weight A and view weight B) to generate respective intermediate image A 102 and intermediate image B 104. For example, in certain implementations, the weighting depends on the sign of the fan angle and on whether both the ray and the conjugate ray through the voxel impact the detector, as discussed below.

Figure 3:
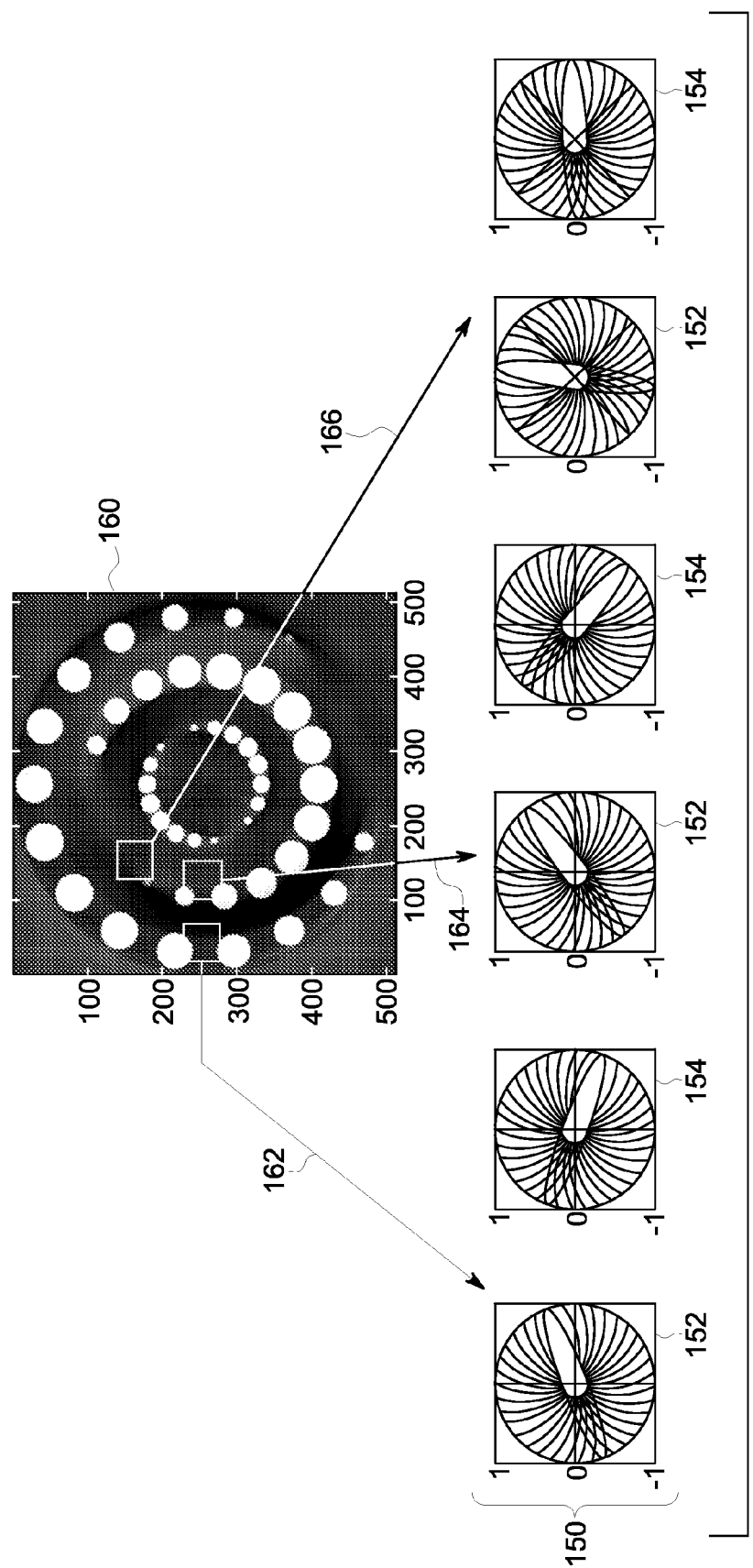
FIG. 3 depicts differing frequency information for differing points in an image and corresponding to separate intermediate reconstructions, in accordance with aspects of the present disclosure.

The respective intermediate images A and B at each view each contain complementary frequency information at each corresponding section of the image, as shown in FIG. 3. In particular, the frequency information 150 corresponding to the respective intermediate image A 102 and intermediate image B 104 (depicted as frequency information A 152 and frequency information B 154) for different points in the image data of a sample image 160 is depicted. The frequency information is viewed as from the "north pole" of a frequency sphere associated with a given voxel at each of the respective points. In this example, the first set 162 and second set 164 of frequencies are located at the same angle relative to the center of the image 160 and the second set 164 and third set 166 of frequencies are located at the same radius, but at different angles from the center of image 160. As will be appreciated, moving radially about the center of the image (as with second frequency set 164 and third frequency set 166) holds views constant but shifts the center frequency. Conversely, moving in or out along a radius but at a common angle (as with first frequency set 162 and second frequency set 164) maintains the center frequency while changing the number of views that fall onto the detector 22 (i.e., "good" views).

With this in mind, and turning back to view weighting steps 98, 100, view weighting can be done in either the projection domain or the image domain. In the depicted example, view weighting is performed in the image domain. If view weighting is done in the image domain, backprojection is only performed once, rather than twice if the view weighting is performed in the projection domain.

The view weighting steps 98, 100 are used to select all views that fall onto the detector 22 and to exclude those views that do not fall on the detector 22 unless there is not at least a half scan of good data in which the views project onto the detector 22. In one embodiment, intermediate image A 102 is reconstructed from one 180° set of projection data and intermediate image B 104 is reconstructed from a different 180° set of projection data, such as a set that is offset by 90° or less from the first set. Though in other embodiments, the offset may be greater than 90°. For example, if all views from a given pixel project onto the detector 22, these two sets of 180° data will be exclusive (and cover the full 360° scan). If there is less than a full scan of data, but more than a half scan (i.e., more than 180°+ the fan angle of the cone X-ray source), the views selected may be offset by another suitable degree, such as 90°.

Figure 4:
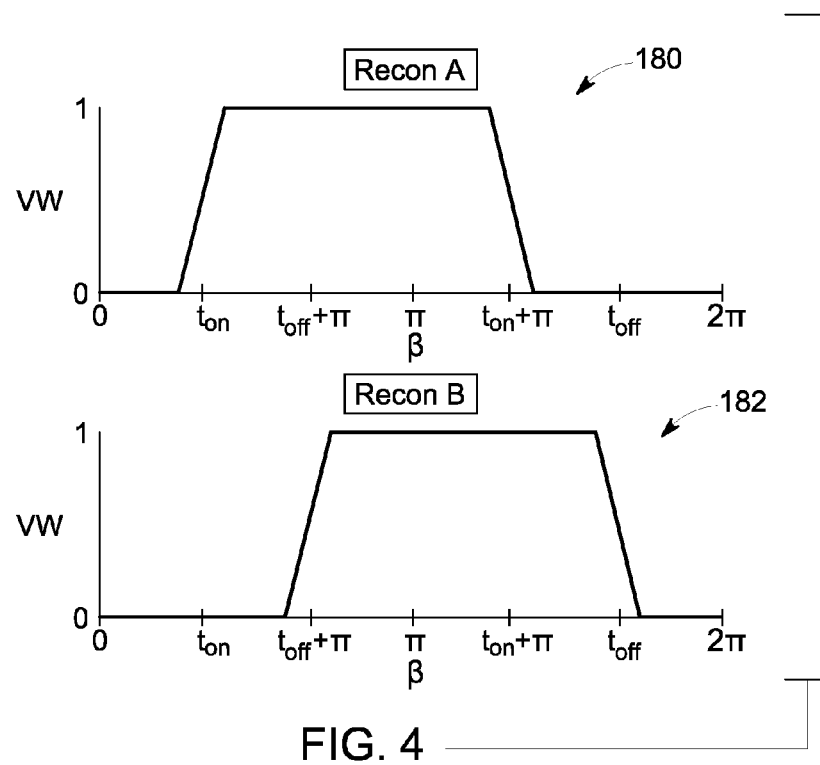
FIG. 4 depicts a differential view weighting scheme in accordance with aspects of the present disclosure.

For example, turning to FIG. 4, one example of a differential view weighting scheme is depicted. In this example, the top graph 180 depicts a view weighting to be applied at block 98 while the bottom graph 182 depicts a view weighting to be applied at block 100, leading to the generation, respectively, of intermediate image A 102 and intermediate image B 104. Each graph in FIG. 4 depicts the view weighting (VW) for a given pixel as a function of radial view. In the depicted example, the view weightings are offset (such as by 90°) radially and include a smooth, as opposed to abrupt, transition from 0 to 1 as a function of β. In other embodiments, other transitions may be employed.

One issue to be addressed is that each pixel will utilize a unique set of views, and the view weighting should account for this in an efficient manner if possible. By way of example, in certain implementations each element of the view weighting function depends on the where the forward ray passes with respect to the Z-axis and whether both the forward ray and its conjugate impact the detector. With respect to the Z-axis aspect, as discussed herein, rays be characterized as being positive or negative with respect to the Z-axis (e.g., to the left of the right of the Z-axis) for the purpose of characterizing and differentiating the forward rays. For example, forward rays passing to the right of the Z-axis, as discussed herein, may be characterized as having a positive angle while forward rays passing to the left of the Z-axis may be characterized as having a negative angle. Thus, in certain implementations a view weighting scheme may be characterized using the angle and the detector impact information such that: (1) if the forward ray path has a positive angle and both the forward ray and its conjugate impact the detector the weight is 0 for the first reconstruction and 1 for the second reconstruction; (2) if the forward ray path has a negative angle and both the forward ray and its conjugate impact the detector the weight is 1 for the first reconstruction and 0 for the second reconstruction; (3) if only the forward ray impacts the detector, the weight is 1 for the first reconstruction and 1 for the second reconstruction; and (4) if only the conjugate ray impacts the detector, the weight is 0 for the first reconstruction and 0 for the second reconstruction. Further, as discussed below, the weights may also be modified to ensure that the effective view weightings for the two different reconstructions are not separated by more than 90° and/or to provide smoothing in the view angle direction.

With the foregoing in mind, the following examples are provided to illustrate certain implementations. With respect to the following example, it should be appreciated that "s" and "t" represent a rotated Cartesian coordinate system that is parallel to the x-y coordinate system. While the x-y coordinate system is fixed with respect to the scanner, the s-t coordinate system rotates with the gantry of the scanner. For example, in the present context, the s coordinate is the signed distance (i.e., displacement) from the z-axis along the direction that is perpendicular to the ray direction, while t is the displacement parallel to the ray direction. With this in mind, in one embodiment, view weightings may be constructed in which, for the first reconstruction (i.e., the reconstruction for which the view weighting of block 98 is applied) the detector 22 or image may be segregated vertically along a line s=0, to the right of which every projection that projects onto the detector 22 is given a view weighting of 1 and every projection that projects off the detector is given a weight of 0. To the left of the line, any pixel whose conjugate projection does not intersect the detector 22 is given a weight of 1 and all other projections are given a weight of 0.

For the second reconstruction (i.e., the reconstruction for which the view weighting of block 100 is applied), the weightings are flipped horizontally with respect to line s such that to the left of line s every projection that projects onto the detector 22 is given a view weighting of 1 and every projection that projects off the detector is given a weight of 0. To the right of the line, any pixel whose conjugate projection does not intersect the detector 22 is given a weight of 1 and all other projections are given a weight of 0.

Figure 5:
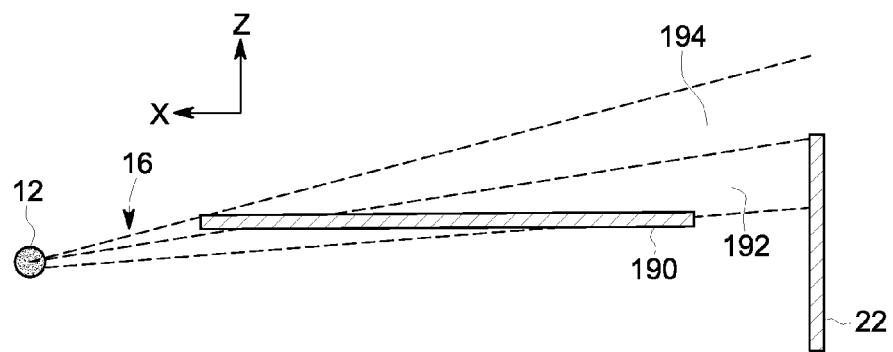
FIG. 5 depicts an image that partially projects on to a detector, in accordance with aspects of the present disclosure.
Figure 6:
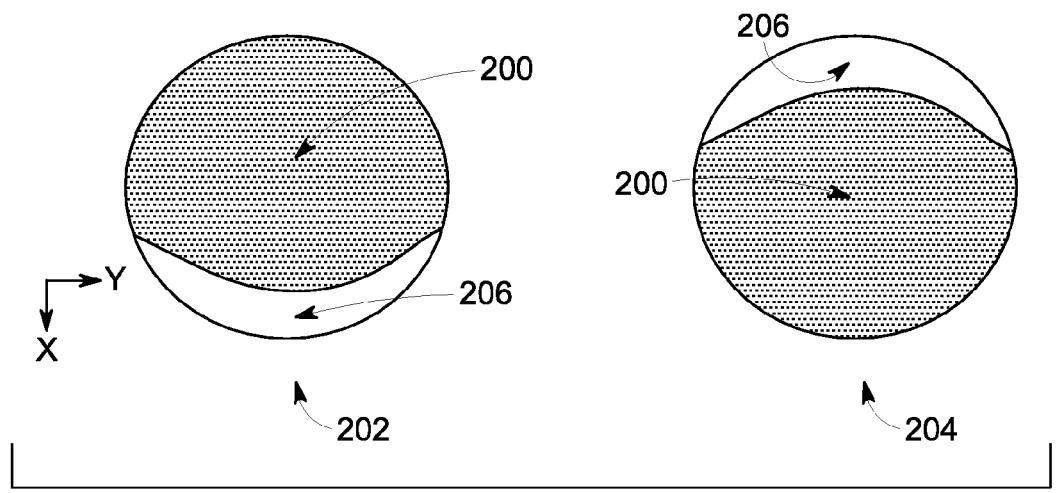
FIG. 6 depicts an image space map of pixels of the image plane of FIG. 5 that project on to the detector at first and second views, in accordance with aspects of the present disclosure.

To further explain the view weighting process, and turning to FIG. 5, an image slice 190 is depicted that partially projects onto the detector 22. That is, a portion 192 of the X-rays passing through slice 190 are incident on a portion of the detector 22, while another portion 194 of the X-rays passing through slice 190 are not incident on the detector 22. With this in mind, FIG. 6 illustrates an image space map of pixels 200 that project onto the detector 22 at a first view 202 (depicted on the left and as seen from the positive Z-direction) and at a conjugate view 204 (on the right). The pixels 206 that do not project onto the detector 22 are also depicted.

Figure 7:
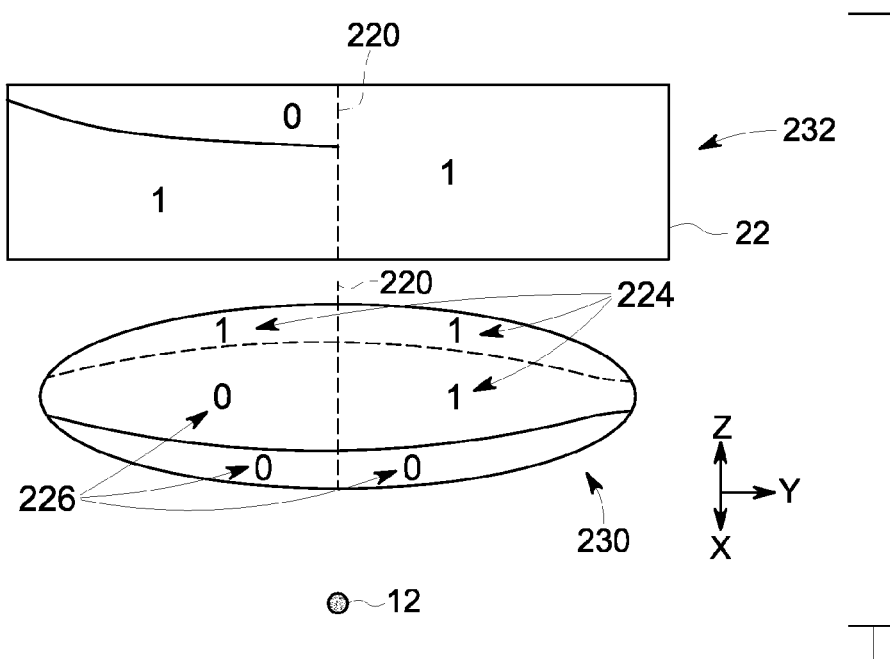
FIG. 7 depicts an example of a first view weighting scheme as seen from an oblique angle, in accordance with aspects of the present disclosure.
Figure 8:
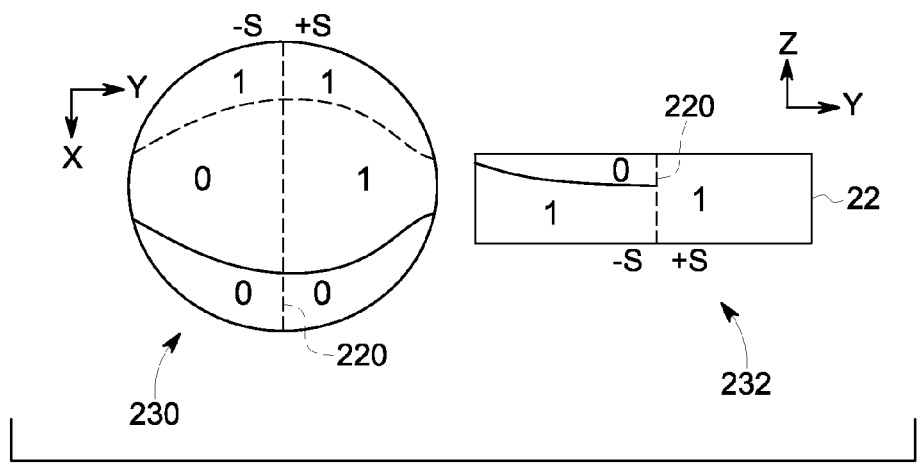
FIG. 8 depicts an example of a first view weighting scheme as seen from a straight-on angle, in accordance with aspects of the present disclosure.

With this in mind, and turning to the view weighting process, FIG. 7 depicts view weighting for the first reconstruction (i.e., block 98) for such an example as seen from an oblique angle, while FIG. 8 depicts the corresponding view weighting straight on, as seen from the positive Z-direction. As set forth in the above example, for projections incident on the detector 22 to the right of line s 220, the view weighting 224 is set to 1. However, to the left of line s 220, if its conjugate doesn't project onto the detector 22, the view weighting 224 is set to 1, otherwise a view weighting 226 is applied that is set to 0. View weightings are depicted in both the image domain 230 and the detector domain 232. The corresponding view weighting scheme as seen straight on (from a positive Z-direction) is seen in FIG. 8 which also depicts the view weightings in the image domain 230 at a respective view for the first reconstruction (i.e., block 98) as well as in the detector domain 230. In this example, to obtain the view weightings for the second reconstruction (i.e., block 100), the respective weightings are simply flipped with respect to line s 220.

The preceding examples are provided to facilitate visualization. As will be appreciated, an image slice 190 located closer to the edge of the detector 22 will have fewer pixels that project on to the detector 22. In certain instances, some of the pixels in the image plane 190 may not even have a half scan (i.e., 180°+ the fan angle) of data that falls on to the detector 22. In such cases, data may be extrapolated to obtain a half scan worth of data for reconstruction.

To generate smooth transitions in the view weighting, and to avoid artifacts attributable to the view weighting, one or more feathering approaches may be employed. For example, in one implementation, Z-smoothing may be employed whereby the view weighting is linearly decreased in the Z-direction from a weight of 1 at 5 rows on the detector 22, to a weight of 0.5 at the edge of the detector 22, to a weight of 0 at 5 rows past the detector 22. Such Z-smoothing may decrease artifacts attributable to view weighting, but may result in discontinuities in the row direction.

In other implementations, angular smoothing may instead be employed. In such implementations, the feathering is proportional to the number of views that are employed for the voxel to transition onto or off of the detector 22. In one example, this approach corresponds directly to weighting each pixel as a function of β, and will ensure that the sum of views adds up to unity when scaled across all pixels. In one implementation, it may be more efficient to handle the image space in polar coordinates as opposed to Cartesian coordinates. In one such case, each radius would have its own transition point onto and off of the detector 22. By calculating at what angle the transition occurs, a simple smooth linear transition may be implemented.

To determine the transition point as a function of radius, the formula describing the transition line (which corresponds to the line in the image plane where the projection hits the edge of the detector 22) in the image space as a function of s and t such that:

$$SourceToIso \cdot \cos\left[\arcsin\left(\frac{s}{SouceToIso}\right)\right] - \frac{offsetZ \cdot SourceToIso}{EdgeOfSDetInZ} = t \quad (1)$$

$$\sqrt{SourceToIso^2 - s^2} - \frac{offsetZ \cdot SourceToIso}{EdgeOfDetInZ} = t \quad (2)$$

$$\sqrt{SourceToIso^2 - r^2 \cdot \cos^2\theta} - \frac{offsetZ \cdot SourceToIso}{EdgeOfDetInZ} = r \cdot \sin\theta \quad (3)$$

$$SourceToIso^2 = r^2 \cdot \sin^2\theta + r^2 \cdot \cos^2\theta + 2 \cdot a \cdot r \cdot \sin\theta + a^2 \quad (4)$$

$$\text{where } a = \frac{offsetZ \cdot SourceToIso}{EdgeOfDetInZ}$$

$$0 = r^2 + 2 \cdot a \cdot r \cdot \sin\theta + a^2 - SourceToIso^2, \text{ and} \quad (5)$$

$$\theta_{transition} = \arcsin\left(\frac{-r^2 - a^2 + SourceToIso^2}{2 \cdot a \cdot r}\right). \quad (6)$$

Computing the line for the conjugate edge of the detector 22 for a given view is accomplished by transforming the t axis to negative t, or, in other words, by flipping it about t=0. Knowing this θ transition then, it should be possible to compute the radius and angle in the image domain of the pixel or detector 22, and to then calculate a linear weight based on the calculated θ transition at that radius, even if in the detector domain.

Turning back to FIG. 2, the preceding discussion is largely related to the view weighting steps applied at blocks 98 and 100. As shown in FIG. 2, having obtained the respective view weighted intermediate images A 102 and intermediate images B 104, the next steps, in the depicted implementation, involve image domain masking. In particular, as discussed below, these steps allow selection (blocks 108, 110) of subdivisions of the respective images that have similar frequency characteristics, so that these selected image subdivisions can be transformed to the frequency domain (blocks 112, 114) and operated on individually. To provide good image quality, transitions between image subdivisions should be smooth, such as a transition that linearly proceeds from 0 to 1 with respect to angle.

Figure 9:
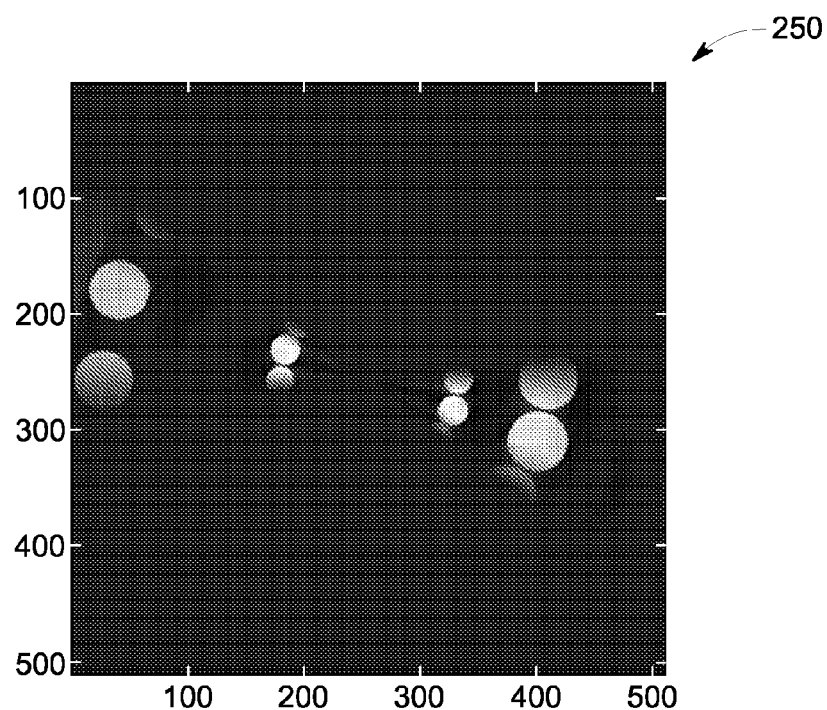
FIG. 9 depicts an example output of an image after spatial domain masking, in accordance with aspects of the present disclosure.

By way of example, FIG. 9 depicts an example output (i.e., masked image 250 or 252 in the parallel track) of the image 160 of FIG. 3 after view weighting (block 98 or 100) and spatial domain masking (block 108 or 110). As depicted, the spatial domain masking step 108, 110 selects out selections of the respective view weighted images for transformation in the frequency domain (blocks 112, 114). For example, turning to FIG. 2, the masked image domain images 250, 252 may be Fourier transformed using a fast Fourier transform at steps 112, 114, respectively.

Figure 10:
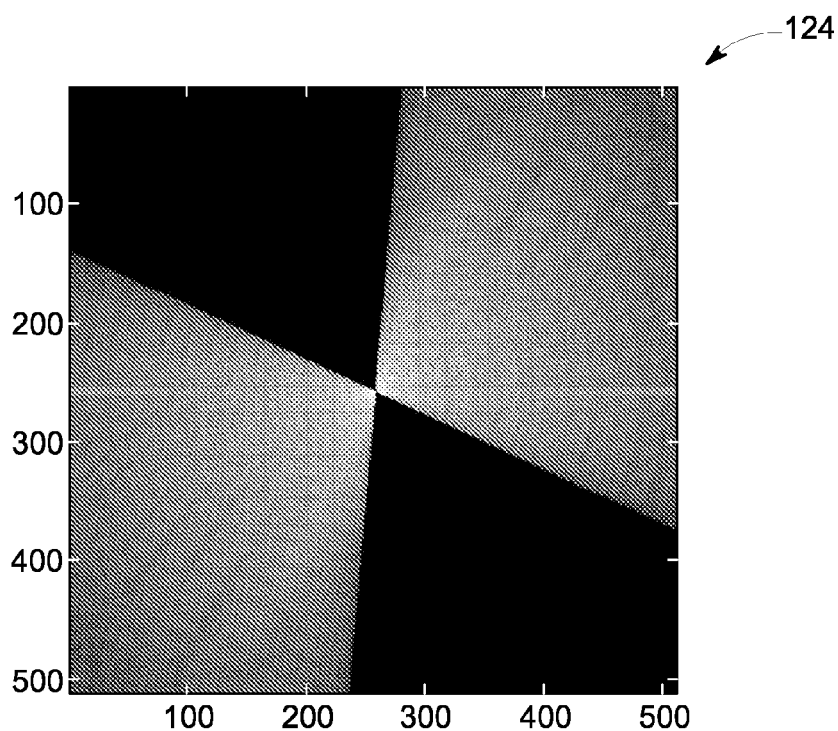
FIG. 10 depicts an example of masked frequency information, in accordance with aspects of the present disclosure.

The output frequency domain representations 116, 118 may also be masked (blocks 120, 122) in the frequency domain to pull out the proper frequency information for each image. As in the preceding masking discussion, a smooth transition region may be provided in these masking steps 120, 122 to reduce or minimize artifacts. Such a smooth transition may be accomplished linearly with respect to angle. As will be appreciated, the proper center of the frequency space is located at a different pixel location than in the spatial domain due to the nature of the fast Fourier transform, and this should be accounted for in the described operations. The angle of the frequency to mask at is the same as the angle of the center good view from the spatial domain. An example of the masked frequency information 124 (or 126 in the parallel track) shown in log scale is depicted in FIG. 10. In FIG. 10, the log scale representation creates the appearance that more than 90° are contributing, however this appearance is due to the feathering applied to smooth transitions, as discussed above.

Figure 11:
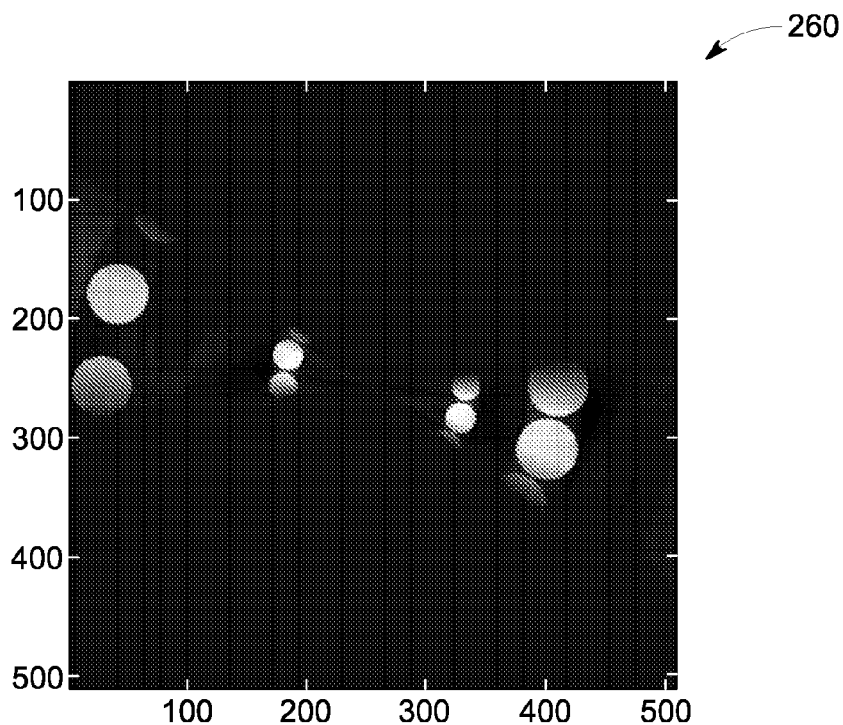
FIG. 11 depicts an example of an image output after inverse fast Fourier transform, in accordance with aspects of the present disclosure.
Figure 12:
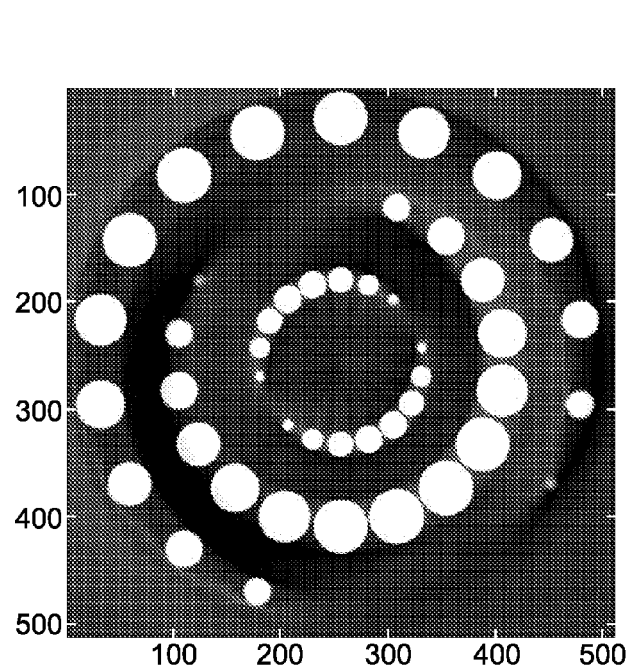
FIG. 12 depicts a final image output of one embodiment of the present approach, in accordance with aspects of the present disclosure.

In the depicted example, the masked frequency information 124, 126 for each reconstruction is added (block 128) together to generate a fully sampled frequency space 130 having contributions only from projections that project on to the detector 22. That is, after proper masking, so that the proper 90° is taken from the first reconstruction, and the proper 90° is taken from the second reconstruction, the frequency images 124, 126 are summed 128, producing a fully sampled frequency space 130 having contributions only from projections that project onto the detector 22. The inverse Fourier transform (block 132) is then applied to transform the frequency information 130 into the spatial domain, i.e., image space, yielding an image output 260 (FIG. 11). As depicted in FIG. 2, the respective image outputs 260 for each subdivision of data are summed (block 140) and scaled to account for padding (e.g., mask operation 142) to produce a final output image 270 (FIG. 12).

In the preceding example of an implementation, an embodiment of an algorithm is described that may be used to reconstruct full scan data acquisitions of a cone-beam CT system, or, more broadly, acquisitions that are greater than 180°+ the fan angle of the cone. In this approach, the view weighing is applied in the projection domain and is performed to allow those regions of the data acquisition consisting of limited amount of complete projection data to only receive backprojection from two offset angular ranges. In this manner, the two sub-reconstructions so generated can be mixed or combined in Fourier space to include only data derived from good projections (i.e., projections that impacted the detector 22). In the preceding example, view weighting is described as being performed in the projection domain to simplify implementation.

In the following example, an implementation employs a view weighting scheme in the image domain which has benefits with respect to image quality, including image uniformity. The image domain view weighting helps to resolve normalization issue that may be associated with projection domain weighting schemes. In one implementation, the image domain weights will be pre-calculated on a polar coordinate system to minimize error from interpolation. Further, in certain embodiments, a maximum of 270° worth of data is used in order to minimize the impact of mishandled data. In addition, weightings may be optimized so as to allow greater use of extrapolation data.

Figure 13:
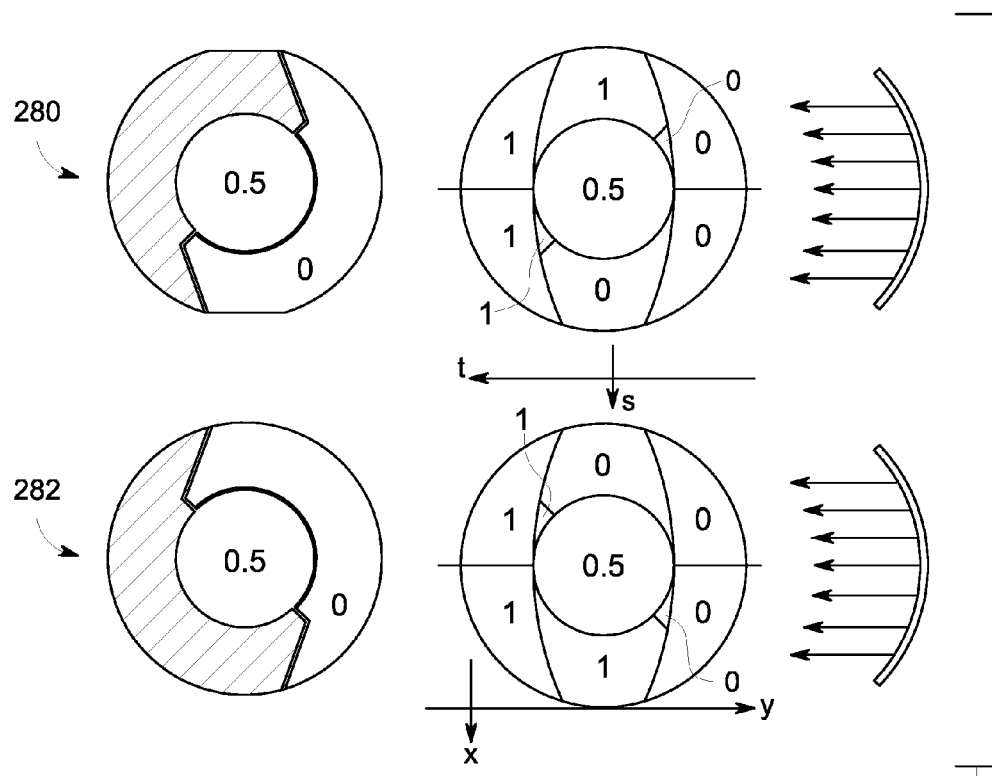
FIG. 13 depicts image domain masks for use in a view weighted backprojection step, in accordance with aspects of the present disclosure.

By way of example, FIG. 13 depicts image domain masks 280, 282 for use in a view weighted backprojection step, in accordance with the present approach. To address normalization issues, the weights are generated in a polar coordinate system and only a half turn of the weight is generated, with the other half of the weight calculated from its conjugate weight, thus assuring normalization in the reconstructions. The weights for the first reconstruction (i.e., mask 280) are generated for a first radial segment (e.g., segment AC) of the acquisition and the weights for the second reconstruction (i.e., mask 282) are generated for a second radial segment (e.g., segment BD) of the acquisition that may overlap with, but be offset from, the first radial segment.

In one implementation, the radial offset between segments AC and BD is 90°. In such an implementation, when the available data for a voxel is greater than 270° (but less that 360°), only 270° of good data (i.e., where projections impacted the detector 22) to achieve suitable reconstruction results. This is shown in FIG. 13 where the combined region of masks 280 and 282 having a weight of 1 corresponds to 270°. In addition, sharp masks may introduce streak artifacts, especially for data with inconsistency (e.g., motion). Consequently, some amount of smoothing may be applied to the weight along θ and Z directions.

In addition, some extrapolated data may be used to improve image quality. The actual contribution for the final reconstruction is from 180, with those data outside of the range only contributing small amount to the low frequency region. Therefore, using small amount of extrapolation data may get rid of shadings.

Figure 14:
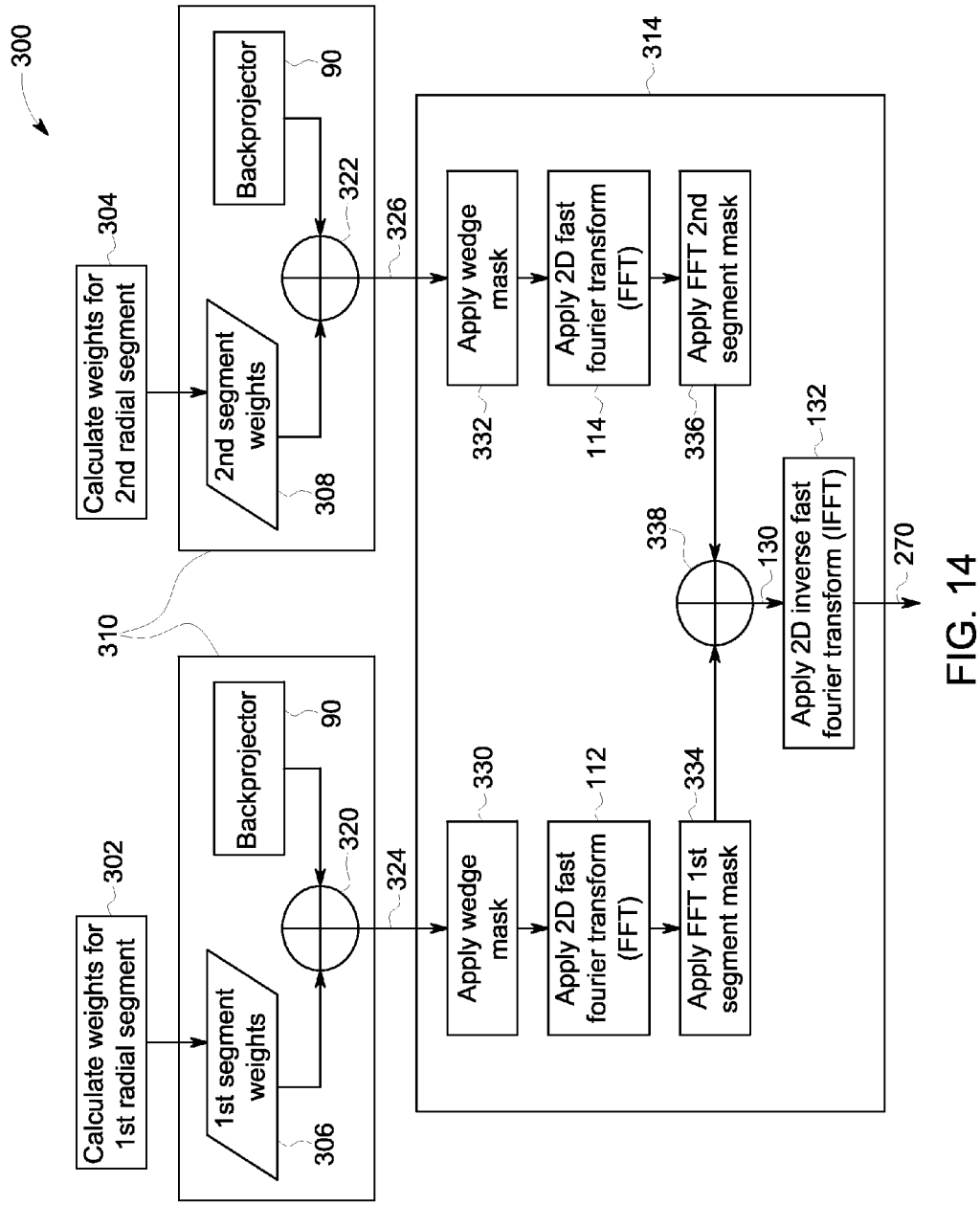
FIG. 14 depicts control flow logic describing an additional embodiment of an algorithm for reconstructing an image, in accordance with aspects of the present disclosure.

Turning to FIG. 14, a generalized flow diagram corresponding to control logic of an algorithm 300 for processing projection data using image domain weighting is depicted. In accordance with the depicted implementation a first set 310 of steps are performed at each view while a second set 314 of subsequent steps are performed at each subdivision of data (e.g., wedge), as discussed below.

In accordance with the depicted implementation, image domain weights 306, 308 (as depicted in FIG. 13) are calculated at each view for a first radial segment (block 302) and a second radial segment (block 304).

In particular, for each view, a backprojection (block 90) of the acquisition sinogram data is performed using the respective 1st radial segment weights 306 or 2nd radial segment weights 308, depending on the respective track. The respective image products are summed across all views for the respective first radial reconstruction (block 320) and second radial reconstruction (block 322) to generate intermediate images 324, 326.

For each subdivision of data (e.g., a 90° wedge) to be processed, a suitable mask (e.g., a wedge mask) is applied (blocks 330, 332) to the respective intermediate images 324, 326 to select out the appropriate subdivision data for transformation to the frequency domain. Transformation of the masked data to the frequency domain is accomplished by applying a respective fast Fourier transform (FFT) 112, 114 to the respective masked image data.

Masks may also be applied (blocks 334, 336) in the frequency domain that are specific to the respective first and second reconstructions and which pull out the proper frequency information for each respective reconstruction. In one embodiment, the masks applied as steps 334, 336 may be configured (e.g., may differ in feathering length) to account for the difference in data availability for voxels at different radii. The respective masked frequency information for each subdivision may be combined or otherwise added (block 338) to generate a fully sampled frequency space 130 having contributions only from projections that project on to the detector 22. The inverse Fourier transform (block 132) is then applied to transform the frequency information 130 into the spatial domain, i.e., image space, yielding a final output image 270.

While the preceding examples describe useful implementations of reconstructing cone-beam CT data, such as an axial scan of such CT data, other modifications may be performed to enhance these implementations. For example, one modification includes using additional half-scan reconstructions (e.g., a third radial segment, such as EF) in addition to the first and second reconstructions based on differing radial segments. In one such embodiment the additional half scan reconstruction may be the half scan reconstruction where the center view is not offset with respect to the respective voxel. That is, the center view of radial segments AC and BD would each be offset with respect to the respective voxel while the center view of respective voxel EF would not be offset with respect to the respective voxel.

In a further embodiment, the subdivision level processing 84, 314 may instead be performed voxel-by-voxel. In one such implementation, instead of a whole image fast Fourier transform (FFT), FFT may only be performed on the respective voxel of interest and the phase term used in the FFT can be pre-calculated.

As will be appreciated by those of ordinary skill in the art, the foregoing examples, demonstrations, and process steps may be implemented by suitable code on a processor-based system, such as a general-purpose or special-purpose computer or an imaging system having such computational components. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code, may be stored or adapted for storage on one or more tangible, machine readable media, such as on memory chips, local or remote hard disks, optical disks (that is, CDs or DVDs), or other media, which may be accessed by a processor-based system to execute the stored code. The tangible media may include paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The various image reconstruction techniques discussed herein provide several advantages, including improved image quality. Among other advantages, the present approaches reduce cone-beam artifacts, which may help in increasing the ability of radiologists to be able to make better decisions based on the images.

The above-description of the embodiments of the method for reconstructing an image and the system for reconstructing an image have the technical effect of improving workflow and diagnostic accuracy by enhancing image quality and reducing image artifacts, thereby allowing acceleration of image processing applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of reconstructing a computed tomography (CT) image, the method comprising:
   acquiring a set of projection data for an imaged volume using a CT imaging system;
   reconstructing at least a first intermediate reconstruction and a second intermediate reconstruction using the acquired set of projection data, wherein the first intermediate reconstruction and the second intermediate reconstruction are reconstructed using different view weightings;
   masking the first intermediate reconstruction and the second intermediate reconstruction to select different subdivisions of image data;
   applying a frequency transform to transform each subdivision of image data to frequency space;
   masking the frequency transform of each subdivision to select frequency information of interest for each of the first intermediate reconstruction and the second intermediate reconstruction;
   for each subdivision, combining the frequency information selected from the first intermediate reconstruction with the frequency information selected from the second intermediate reconstruction to generate a fully sampled frequency space; and
   applying an inverse frequency transform to the fully sampled frequency space to generate a final image volume.

2. The method of claim 1, wherein the set of projection data is acquired over 360°.

3. The method of claim 1, wherein the first intermediate reconstruction and the second intermediate reconstruction comprise complementary frequency information.

4. The method of claim 1, wherein the different view weightings are determined based on where a forward ray passes with respect to a Z-axis and whether both the forward ray and a conjugate ray through a voxel impact a detector of the CT imaging system.

5. The method of claim 4, wherein the view weightings transition from 0 to 1 linearly.

6. The method of claim 1, wherein the different view weightings are applied in a projection domain.

7. The method of claim 1, wherein the different view weightings are applied in an image domain.

8. The method of claim 1, wherein reconstructing the first intermediate reconstruction comprises reconstructing a first set of 180° projection data and reconstructing the second intermediate reconstruction comprises reconstructing a second set of 180° projection data that is radially offset from the first set of 180° projection data.

9. The method of claim 8, wherein the second set of 180° projection data is radially offset from the first set of 180° projection data by 90°.

10. The method of claim 8, wherein the second set of 180° projection data is radially offset from the first set of 180° projection data by less than 90°.

11. The method of claim 1, wherein the fully sampled frequency space comprises only contributions from projections that impact a detector of the CT imaging system.

12. The method of claim 1, wherein acquiring a set of projection data comprises performing an axial scan using a cone-beam X-ray emission.

13. A non-transitory, computer-readable medium configured to store one or more routines executable by a processing system, the routines, when executed, causing acts to be performed comprising:
accessing a set of axial CT projection data;
reconstructing a first intermediate reconstruction using the set of axial CT projection data and a first view weighting;
reconstructing a second intermediate reconstruction using the set of axial CT projection data and a second view weighting that differs from the first view weighting;
selecting, from the first intermediate reconstruction and the second intermediate reconstruction, a plurality of subdivisions of data corresponding to different portions of a final image to be reconstructed;
transforming the plurality of subdivisions of data into corresponding frequency representations;
masking the frequency representations to select frequency information of interest for each of the first intermediate reconstruction and the second intermediate reconstruction;
combining the selected frequency information from the first intermediate reconstruction and the second intermediate reconstruction to generate a fully sampled frequency space for each subdivision; and
applying an inverse frequency transform to the fully sampled frequency space to generate the final image.

14. The non-transitory, computer-readable medium of claim 13, wherein the first intermediate reconstruction and the second intermediate reconstruction comprise complementary frequency information.

15. The non-transitory, computer-readable medium of claim 13, wherein the first view weighting and the second view weighting are derived based on where a forward ray passes with respect to a Z-axis and on whether both the forward ray and a conjugate ray through a voxel impacts a detector used to acquire the axial CT projection data.

16. The non-transitory, computer-readable medium of claim 13, wherein reconstructing the first intermediate reconstruction comprises reconstructing a first set of 180° CT projection data and reconstructing the second intermediate reconstruction comprises reconstructing a second set of 180° CT projection data that is radially offset from the first set of 180° CT projection data by 90° or less.

17. A computed tomography (CT) imaging system, comprising:
a source of X-ray emissions;
a detector positioned opposite from the source with respect to an imaging volume, wherein the detector is configured to generate signals in response to the X-rays, when emitted;
a rotational positioning system configured to rotate the source and the detector about the imaging volume;
a detector acquisition system configured to acquire the signals generated by the detector;
a memory storing one or more routines; and
a processing component configured to access the signals from the data acquisition system and to execute the one or more routines stored in the memory, wherein the one or more routines, when executed by the processing component, cause acts to be performed comprising:
reconstructing at least a first intermediate reconstruction and a second intermediate reconstruction using the signals acquired by the detector acquisition system, wherein the first intermediate reconstruction and the second intermediate reconstruction are reconstructed using different view weightings;
dividing the first intermediate reconstruction and the second intermediate reconstruction into corresponding subdivisions of data;
applying a fast Fourier transform to transform each subdivision of image data to frequency representations;
combining selected frequency information from the first intermediate reconstruction with the selected frequency information from the second intermediate reconstruction to generate a fully sampled frequency space for each subdivision; and
applying an inverse fast Fourier transform to the fully sampled frequency space to generate a final image volume.

18. The CT imaging system of claim 17, wherein the signals acquired by the detector acquisition system are acquired over a 360° rotation of the source and detector about the imaging volume.

19. The CT imaging system of claim 17, wherein the first intermediate reconstruction and the second intermediate reconstruction comprise complementary frequency information.

20. The CT imaging system of claim 17, wherein the different view weightings are derived based on where a forward ray passes with respect to a Z-axis and on whether both the forward ray and a conjugate ray through a voxel impacts the detector.

21. The CT imaging system of claim 17, wherein reconstructing the first intermediate reconstruction comprises reconstructing a first set of 180° projection data and reconstructing the second intermediate reconstruction comprises reconstructing a second set of 180° projection data that is radially offset from the first set of 180° projection data.

* * * * *